(12) United States Patent
Grünig

(10) Patent No.: US 7,637,327 B2
(45) Date of Patent: Dec. 29, 2009

(54) PERCUSSIVE TOOL, IN PARTICULAR FOR SURGICAL USE

(75) Inventor: Daniel Grünig, Schwarzenberg (CH)

(73) Assignee: Grünig & Elminger AG, Malters (CH)

( * ) Notice: Subject to any disclaimer, the term of this patent is extended or adjusted under 35 U.S.C. 154(b) by 97 days.

(21) Appl. No.: 11/920,404

(22) PCT Filed: May 17, 2005

(86) PCT No.: PCT/CH2005/000274

§ 371 (c)(1),
(2), (4) Date: Jan. 7, 2008

(87) PCT Pub. No.: WO2006/122435

PCT Pub. Date: Nov. 23, 2006

(65) Prior Publication Data

US 2008/0245541 A1   Oct. 9, 2008

(51) Int. Cl.
*B23Q 5/00* (2006.01)
(52) U.S. Cl. .............................. 173/90; 173/91; 227/10; 227/130; 227/120
(58) Field of Classification Search ............... 173/90, 173/91; 227/10, 130, 120, 2
See application file for complete search history.

(56) References Cited

U.S. PATENT DOCUMENTS

| | | | | |
|---|---|---|---|---|
| 1,264,318 A * | 4/1918 | McGrath, J.T. | ............... | 91/229 |
| 3,891,036 A * | 6/1975 | Schmidt | ..................... | 173/91 |
| 4,651,833 A * | 3/1987 | Karpf et al. | .................. | 173/136 |
| 4,840,237 A * | 6/1989 | Roemer | ........................ | 175/19 |
| 4,886,128 A * | 12/1989 | Roemer | ........................ | 175/19 |
| 5,057,112 A * | 10/1991 | Sherman et al. | ............... | 606/79 |
| 5,152,352 A | 10/1992 | Mandanis | ..................... | 173/17 |
| 5,485,887 A | 1/1996 | Mandanis | ..................... | 173/17 |
| 5,913,860 A | 6/1999 | Scholl | ......................... | 606/100 |
| 6,319,270 B1 | 11/2001 | Grafton et al. | .............. | 606/232 |

FOREIGN PATENT DOCUMENTS

| | | |
|---|---|---|
| DE | 168700 | 3/1906 |
| DE | 89 11 061.7 | 10/1989 |

(Continued)

OTHER PUBLICATIONS

International Search Report for PCT/CH2005/000274.

*Primary Examiner*—Brian D Nash
(74) *Attorney, Agent, or Firm*—Ohlandt, Greeley, Ruggiero & Perle, LLP; George W. Rauchfuss, Jr.; Charles N. J. Ruggiero

(57) ABSTRACT

The invention relates to a percussive tool having an oscillatory drive (3), the force of which is transmitted to a tool bit holder (25) by way of a drive member (17). Extending through the percussive tool is a longitudinal opening that allows a rod-shaped object, such as, for example, a guide wire, to be guided through the percussive tool. The tool bit holder (25) has a seat (34), which can receive the tool bit in different orientations. Moreover, the tool bit holder (25) is made of a combination of light metal and steel, which allows a reduction in acceleration forces and noise generation. A saddle-shaped coupling (24) is provided between the tool bit holder (25) and the drive member (17), which guarantees a tight fit.

17 Claims, 4 Drawing Sheets

FOREIGN PATENT DOCUMENTS

| | | |
|---|---|---|
| DE | 91 00 115.3 | 3/1991 |
| DE | 198 60 569 C1 | 8/2000 |
| DE | 102 33 694 A1 | 2/2004 |
| EP | 597 547 A1 | 5/1994 |
| EP | 1 270 951 A1 | 1/2003 |
| GB | 562138 | 6/1944 |
| WO | WO 88/02246 | 4/1988 |
| WO | WO 03/097945 | 11/2003 |

* cited by examiner

PERCUSSIVE TOOL, IN PARTICULAR FOR SURGICAL USE

BACKGROUND

The invention is related to a percussive tool, in particular for surgical use, as well as a tool bit holder for such a percussive tool, in accordance with the preamble of the independent claims.

PRIOR ART

A percussive tool of this kind is described in EP 617 926. It comprises a drive part and a tool bit holder. The drive part exerts oscillatory forces, acting in an axial direction, on the tool bit holder.

Such a percussive tool can be used, for example, for operating a bone rasp or a similar surgical tool. However, it may also be employed for driving in a bone nail or another implant. For reasons of simplicity, such an implant will also be referred to in the present text as a "tool bit."

The vibrations generated by the drive part lead to strong mechanical load on the tool bit holder and it is important that the tool bit holder is constructed in such a way that it is able to withstand durably the forces that arise.

In addition, it is also of advantage if the tool is constructed in such a way that the axial forces are transmitted to the tool bit as linearly and as free of torsion as possible.

When the tool bit is used to drive in a bone nail or a similar implant, the procedure is often conducted so that, first, a wire or another thin, rod-shaped structural part is driven into the bone undergoing surgery. The bone nail, which has an axial opening, is then inserted, the wire being guided through the axial opening of the bone nail. In this case, the wire serves as guide for the bone nail. It emerges from the proximal side of the bone nail and is guided around the percussive tool. After the implant has been inserted, the wire is withdrawn.

DESCRIPTION OF THE INVENTION

Posed in a first aspect of the invention is the problem of providing a percussive tool of the above-mentioned kind, which is particularly suited for inserting bone nails and similar implants.

This problem is solved by the percussive tool according to claim 1. A through longitudinal opening is thus provided, which extends in the axial direction from the front side of the percussive tool to the back side thereof through the tool bit holder and the drive part. This longitudinal opening is suited for guiding a rod-shaped component, such as, for example, the wire for guiding the implant, through the percussive tool. The handling of the wire is thereby simplified, because it no longer needs to be guided around the tool.

Posed in a second aspect of the invention is the problem of transmitting the force from the drive part onto the tool bit holder as efficiently as possible.

This problem is fulfilled by the second independent claim. In accordance therewith, the drive part is linked to the tool bit holder through a coupling. The coupling comprises a first part and a second part, with either the first part being arranged on the drive part and the second part on the tool bit holder or the first part on the tool bit holder and the second part on the drive part. The first part tapers outward (that is, in the axial direction toward the second part), whereas the second part is seated on the first part and expands outward (that is, in the axial direction toward the first part), so that, under axial tension, the second part is spread apart by the first part. A tension member for linking the two parts is provided for producing the axial tension. This arrangement allows a fit that is free of play and ensures a good transmission of force onto the tool bit holder.

Posed in a third aspect of the invention is the problem of providing a percussive tool bit that can be simply inserted.

This problem is solved according to a third main claim in such a way that the tool bit holder has an orifice opening and a seat arranged on the orifice opening, which serves to receive a tool bit. The seat has a receiving face that is perpendicular to the axial direction, from which, symmetrically to the orifice opening, at least four raised parts project frontally over the receiving face. There remains space between the raised parts for receiving the shoulders of the tool bit. Through the symmetrical arrangement of at least four such raised parts, a total of at least four depressions are formed between the raised parts and these are suitable for receiving the shoulders of the tool bit. Accordingly, the tool bit can thus be mounted in different positions.

Posed in a fourth aspect of the invention is the problem of providing a percussive tool that runs quietly.

This problem is solved by the fourth main claim in that the tool bit holder has a central body made of light metal, a front terminal part made of steel, and a rear terminal part made of steel. Owing to the use of a central body made of light metal, it is possible to reduce the weight of the tool bit holder. Noise generation is also reduced. In order to be able to carry the forces that arise toward the rear (that is, toward the drive part) and toward the front (that is, toward the tool bit), the two terminal parts are made of steel, because light metal would have only a limited capacity to meet the loads existing in these regions.

The invention also relates to a correspondingly designed tool bit holder.

The terms "toward the front" or "front side" and "toward the rear" or "rear side" are to be understood in the present text and in the claims in such a manner that "toward the front" or "front side" identifies the side of the tool bit held by the tool bit holder and "toward the rear" or "rear side" refers to the side of the mechanism facing away from the tool bit.

BRIEF DESCRIPTION OF THE DRAWINGS

Additional embodiments, advantages, and applications of the invention ensue from the dependent claims and from the description that follows on the basis of the figures. Shown therein are:

PATHS FOR IMPLEMENTATION OF THE INVENTION

Figure 1:
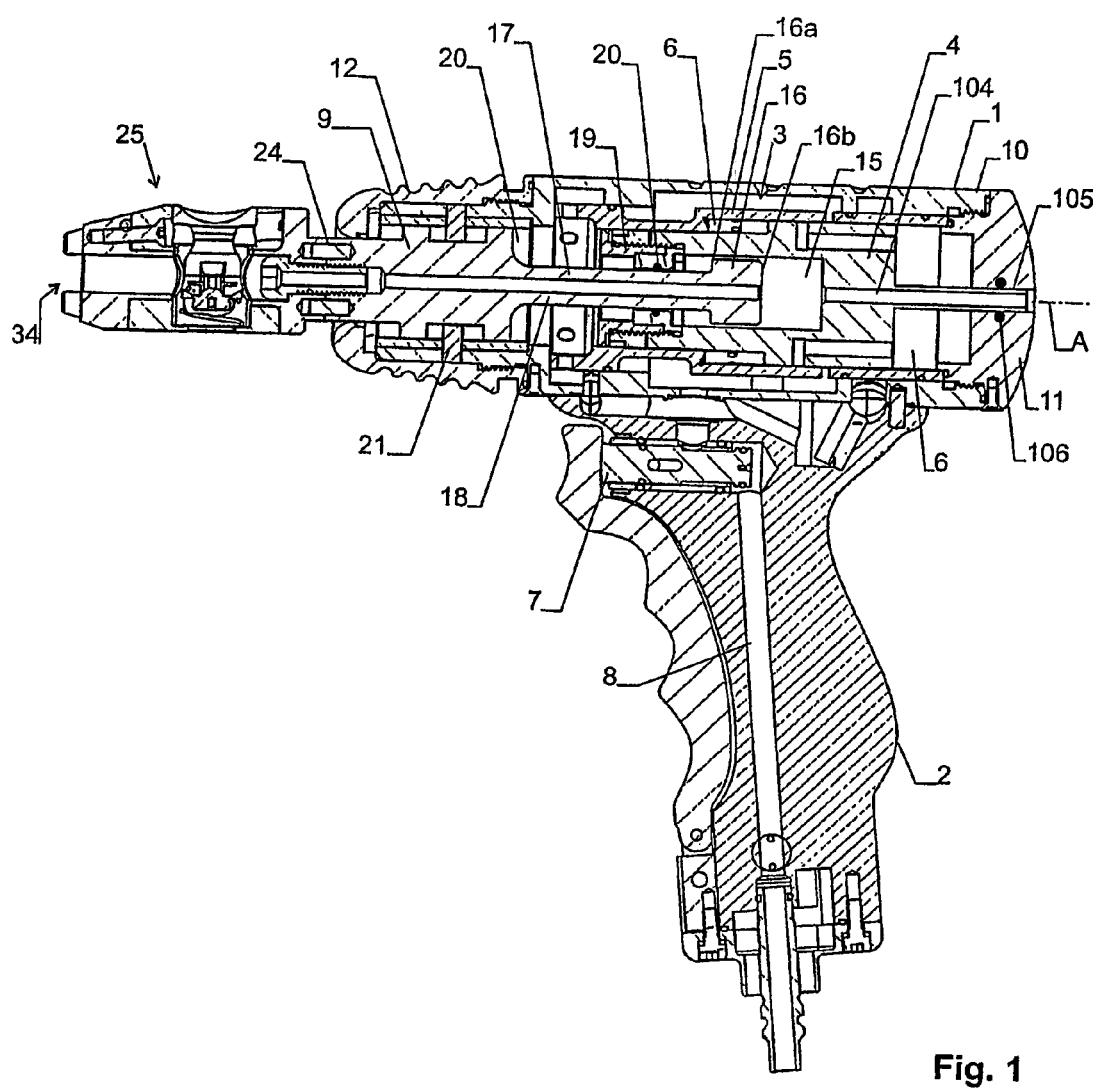
FIG. 1, a section through the entire percussive tool along its longitudinal axis, FIG. 2, a plan view of the tool bit holder and drive member, FIG. 3, a section along line A-A of FIG. 2, FIG. 4, a section along line B-B of FIG. 2, FIG. 5, a section along line C-C of FIG. 2, FIG. 6, a section along line D-D of FIG. 2, FIG. 7, a exploded illustration of the tool bit holder and drive member, FIG. 8, a view of the front terminal part of the tool bit holder as seen obliquely from in front, FIG. 9, a section through the central body of the tool bit holder along line B-B of FIG. 2, FIG. 10, a view of the rear terminal part of the tool bit holder, as viewed obliquely from behind, and FIG. 11, a view of the drive member, as viewed obliquely from in front.
Figure 2:
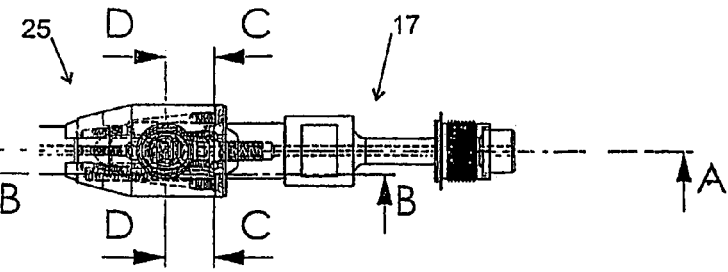

FIG. 1 shows an advantageous embodiment of the percussive tool according to the invention. The tool comprises a housing 1 with a handle 2. Accommodated in the housing 1 is a drive part 3. This comprises a piston 4, which is movably arranged in a cylinder 5. The piston 4 is situated movably in a cylinder chamber 6. When a compressed air valve 7 is operated, compressed air is supplied via a line 8 and sets the piston 4 in oscillatory motion along the longitudinal axis A of the tool. Corresponding drives are known to the practitioner. Because the precise function of the drive is not a subject of the present invention, reference is made to an exemplary embodiment in EP 617 926. In pace of a pneumatic drive, a hydraulic drive or an electromagnetic drive is also conceivable.

The housing 1 has a wall 10, which surrounds the cylinder chamber 6 and to which a back wall 11 on the back end and a cap 12 in the front are screwed.

Arranged in the piston 4 is a cavity 15, in which an enlargement 16 of a drive member 17 engages. The enlargement 16 is tightly linked to a rod 18 of the drive member 17. The rod 18 is guided through a screwed closure 19 having a seal 20, which projects into the front end of the cavity 15.

At its front end, the rod 18 is transformed into a guide block 9 of the drive member 17, which is movably guided in the axial direction A in a chamber 20 in the front cap 12. The axial movement of the drive member 17 is limited by a stationary stopper 21, which engages in a groove in the guide block 9.

At the front end, the drive member 17 is linked by way of a coupling 24 to a tool bit holder 25, which serves to fasten in place a tool bit. Owing to the coupling 24, the tool bit holder 25 can be replaced without disassembling the tool.

The functional operation of the tool described corresponds to that according to EP 617 926. Through the oscillatory back and forth movement of the piston 4, oscillatory forces are exerted along the axial direction A on the enlargement 16 in the form of percussions. In so doing, the front surface 16a and the rear surface 16b of the enlargement 16 are impacted alternately, so that the drive member 17 is moved back and forth.

The oscillatory forces are transmitted from the drive member 17 onto the tool bit holder 25 and from there onto the tool bit inserted in the tool bit holder.

In the following, the individual components of the percussive tool will be described in detail.

The construction of the tool bit holder 25 and of the drive part 17 is illustrated in FIG. 2-7.

The tool bit holder 25 comprises three main parts, namely, a central body 30 made of light metal, a front terminal part 31 made of steel, and a rear terminal part 32 also made of steel. The central body 30 consists primarily of aluminum and/or magnesium and/or titanium, aluminum being advantageous for reasons of cost.

At the front end of the tool bit holder 25, the front terminal part 31 forms a seat 34 for receiving of the tool bit 35 in a rotationally rigid manner, only the rearmost part of the tool bit 35 being illustrated in each case in FIG. 2-7. Extending out from the seat 34 in the axial direction into the tool bit holder 25 is an orifice opening 36. It serves for receiving a rear, rod-shaped part 37 of the tool bit 35

Figure 7:
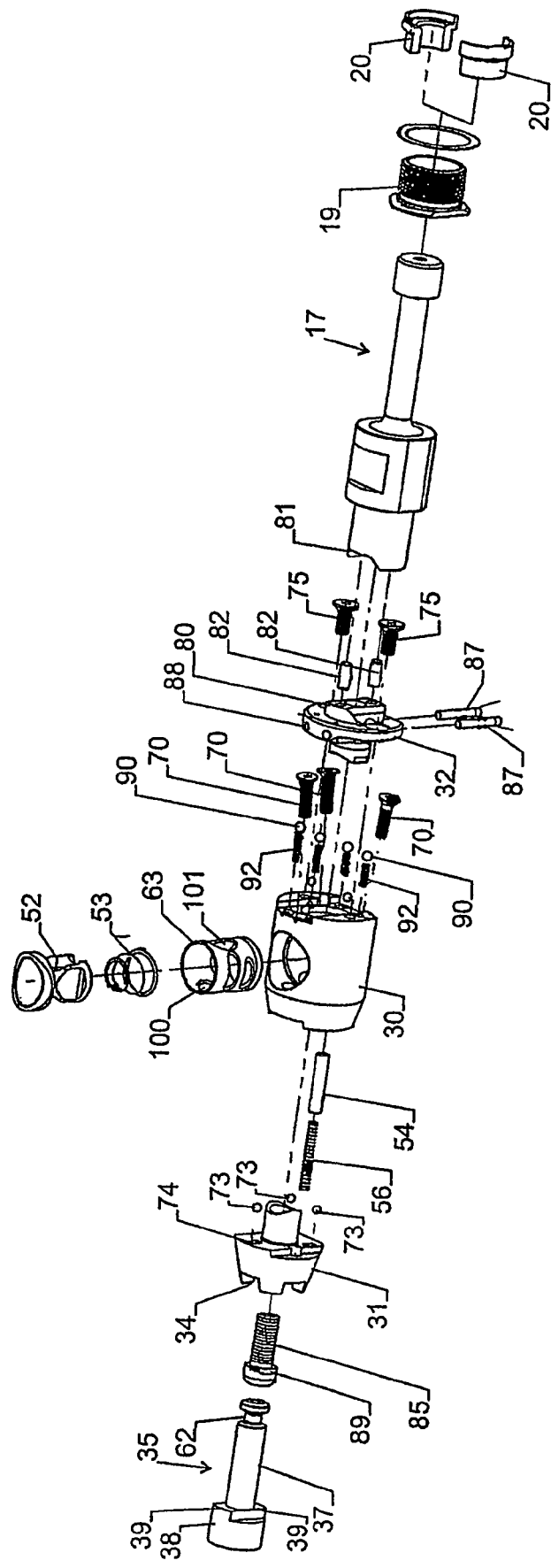

As can be particularly well seen in FIG. 7, the rod-shaped part 37 of the tool bit transforms into a broadened tool bit segment, 38, at its front end, forming two shoulders 39 that project laterally from the rod-shaped part 37. When the tool bit 35 is inserted, its shoulders are received in a rotationally rigid manner by the seat 34.

Figure 8:
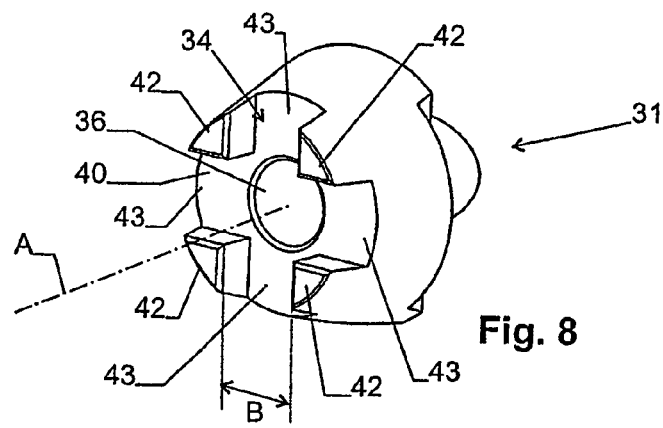
Figure 9:
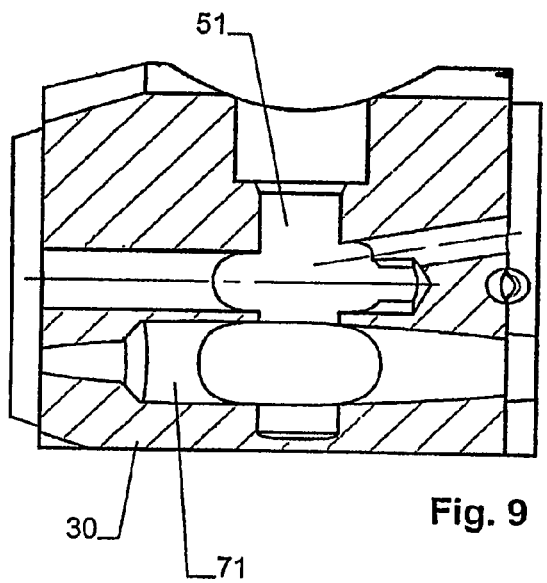

The construction of the seat 34 chosen here can be seen especially clearly in FIG. 8. As illustrated, the seat 34 has a receiving face 40 that is perpendicular to the axial direction A, by means of which impact forces of the tool bit holder 25 can be transmitted to the rear terminal surfaces of the shoulders 39.

Projecting frontally in the axial direction A above the receiving face 40 are at least four raised parts 42, arranged symmetrically around the orifice opening 36. Formed between the raised parts 42 in this way are at least four symmetrical depressions 43, which can received the shoulders 39 of the tool bit 35 in a rotationally rigid manner.

For the embodiment with four, roughly triangular raised parts 42, shown in FIG. 8, the four depressions 43 form two grooves, which are mutually perpendicular and perpendicular to the axial direction A and which intersect in the region of the orifice opening 36. The tool bit 35 can be inserted into these grooves in a total of four different positions.

Preferably, the distance B between neighboring raised parts 42 is approximately 10.05+/−0.02 mm. This corresponds to the width of the shoulders of standardized tool bits in the surgical field.

Figure 3:
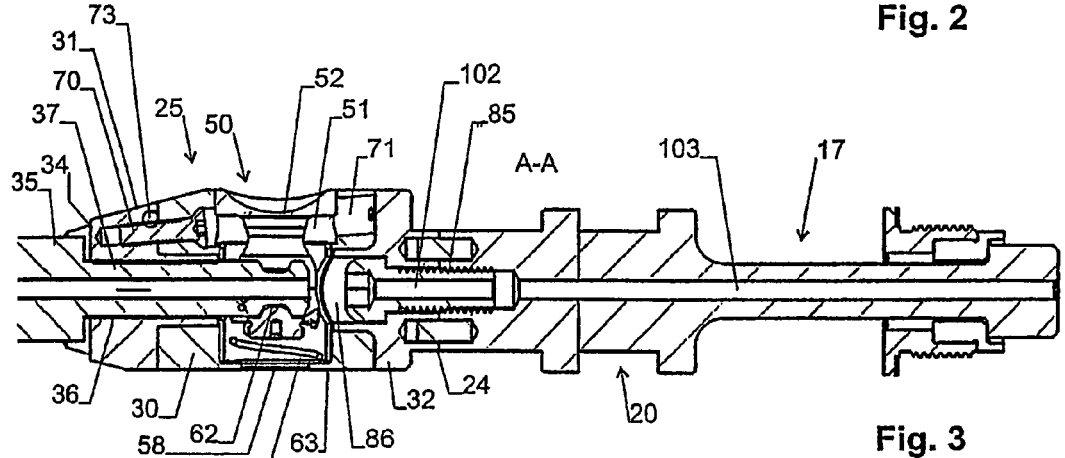
Figure 4:
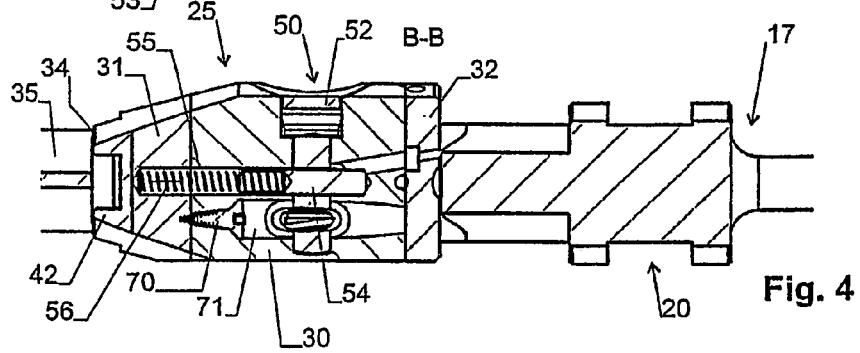

As can be seen particularly in FIG. 3, the rod-shaped part 37 of the tool bit 35 extends through the orifice opening 36 into the central body 30. There it is held in place by a holding mechanism 50. To this end, holding mechanism 50 is furnished with a holding element 52 arranged in a chamber 51 of the central body 30. The holding element 52 can be moved in the chamber 51 transverse to the longitudinal axis A (see FIG. 2) against the force of a conical spring 53. To this end, the chamber 51 is open outwardly on one side and the spring 53 abuts against second side of the chamber 51. The holding mechanism 50 or the holding element 52 is retained against the force of the spring 53 by a pin 54. The pin 54 is situated in a blind hole 55 of the central body 30 and a spring 56 impinges on it. The blind hold 55 opens into the partition between the central body 30 and the front terminal part 31, so that the pin 54 is trapped in the blind hole 55 and can be withdrawn from the blind hole 55 only after separation of the central body 30 and front terminal part 31. As can be seen particularly in FIG. 6, the pin 54 abuts against a catch 57 of the holding element 52 and holds the latter firmly in place against the force of the spring 53.

The chamber 51 has a second opening 58 in the region of the spring 53, through which a cleaning of the chamber is facilitated.

The holding element 52 has a central opening 60 (see FIG. 6), the rim 6 of which engages in a groove 62 (see FIG. 7) in the rod-shaped part 37 of the tool bit 35 and holds it in place. In order to release the tool bit, the holding element 52 need simply be pressed into the chamber 51 against the force of the spring 53.

Arranged in the chamber 51 between the holding mechanism 50 or the holding element 52 and the central body 30 is a thin metal jacket 63. This distributes the forces produced by the holding element 52 onto the light metal of the central body 30 and prevents it from being damaged.

The central body 30 and the front terminal part 31 are fastened together by means of three screws 70 (see FIG. 3, 4, 7). The screws 70 are positioned in angled holes 71 of the central body.

So that the screws 70 cannot become loose during operation of the tool, fixing elements 73, made of plastic, for example, are provided. The fixing elements 73 are seated in depressions 74 (FIG. 7) of the front terminal part 31, adjacent to the holes for the threads of the screws 70. The depressions 74 are to be dimensioned in such a way that the fixing elements 73, in relaxed state, protrude slightly above the depressions and, when the screws 70 are tightened, are deformed by the central body 30 and thereby pressed against the screws 71.

Figure 5:
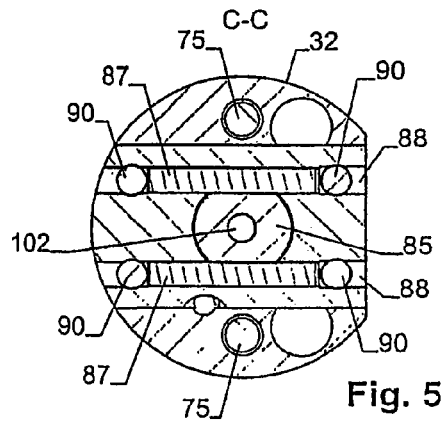
Figure 6:
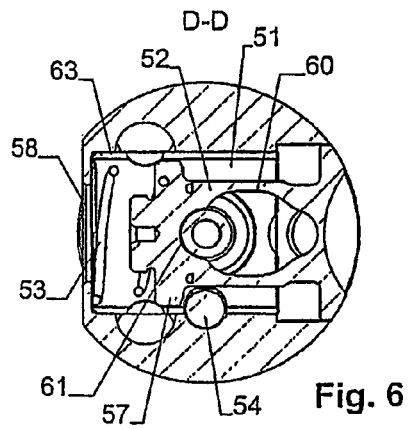

Provided for fastening in place the rear terminal part 32 of the central body 30 are two screws 75 (FIG. 5, 7). The heads thereof lie in two depressions 76 (FIG. 10) in the back side of the rear terminal part 32 and are positioned in such a way that they are partially covered and held tightly in place by the front end of the mounted drive member 17, so that, during operation, they remain fixed in position.

Figure 10:
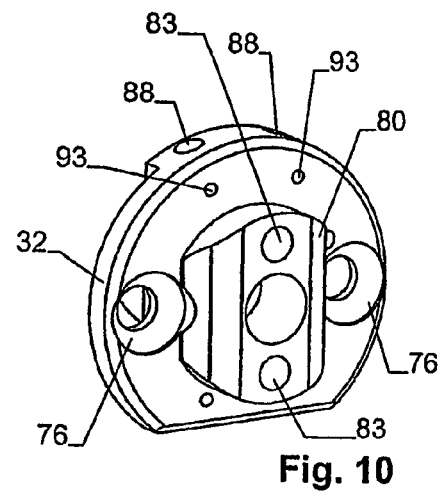
Figure 11:
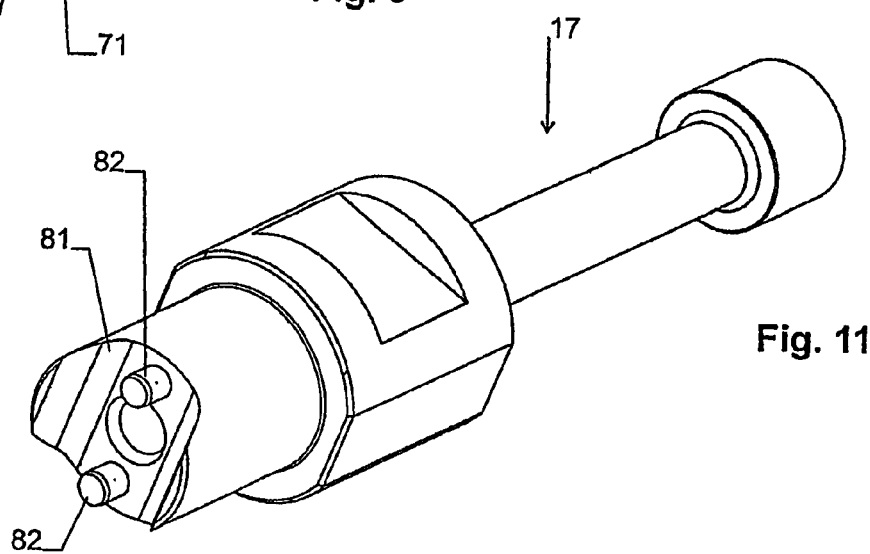

The coupling 24 between the tool bit holder 25 and the drive member 17 comprises, as mentioned at the beginning, a first part and a second part, which mutually engage. In the present example, the first part is arranged at the rear end of the tool bit holder 25 and is formed by a rearward tapering saddle 80 of the rear terminal part 32 (FIGS. 7 and 10). In the present example, the second part is formed by the front end of the drive member 17 and has the form of a rider 81 (FIGS. 7 and 11) that sits on the saddle 80 and the form of which is adapted thereto. Additionally held in the rider 81 are two coupling pins 82, which engage in the holes 83 (FIG. 10) of the rear terminal part and thus form an interlocking linkage of the two parts, which also opposes movement in the longitudinal saddle direction.

Accordingly, the coupling 24 forms a link that is interlocking with respect to rotation around the longitudinal axis A and movement perpendicular to the longitudinal axis A.

Further provided for fastening the tool bit holder 25 on the drive member 17 is a tension member in the form of a coupling screw 85. The head thereof is seated in a depression 86 (FIG. 3) of the rear wall of the chamber 51 and its threaded shaft engages through the coupling 24 into an axial boring of the drive member 17. It thus pulls the drive member 17 against the tool bit holder 25. In so doing, the rider 81 is spread apart somewhat on the saddle 80, so that a stable, play-free linkage results.

The coupling screw 85 is formed by two retaining elements in the form of retaining pins 87 (FIG. 5, 7). These are situated in pin holes 88 (FIG. 5, 7, 10) of the rear terminal part 32. They traverse two lateral recesses 89 in the head of the coupling screw 85 and thus prevent a rotation of the latter in an interlocking manner.

The retaining pins 87 are held in the pin holes 88 of the spherical pin locks 90. Each of the pin locks 90 is situated in its lock hole, which extends from the front side of the rear terminal part 32. Each lock hole intersects one of the pin holes 88 and tapers there in order to form a seat for one of the pin locks 90. Further arranged in each lock hole is a spring 92 (FIG. 7) so as to press the respective pin lock 90 against its seat. In order to prevent the pin lock 90 from becoming loose, each lock hole extends with reduced diameter to an opening 93 (FIG. 10) in the rear end face of the rear terminal part 32, through which a slide lug can be inserted in order to press the pin lock 90 forwards out of the pin hole 88 against the force of the spring 92.

The drive member 17 is constructed in one piece and extends from the tool bit holder 25 into the drive part 3, so that a smooth transmission of force without torsional components is ensured.

As already mentioned in the beginning, it is advantageous to provide a longitudinal opening that extends from the front side of the percussive tool to the back side thereof. It serves to guide a guide wire or the like through the tool.

The longitudinal opening begins at the orifice opening 36, passes through a front opening 100 (FIG. 7) in the steel jacket 63, the central opening 60 of the holding element 52, a rear opening 101 in the steel jacket 63, a longitudinal bore 102 (FIG. 3) of the coupling screw 85, and a longitudinal bore 103 of the drive member 17 (FIG. 3). From there, the longitudinal opening extends through the cavity 15 (FIG. 1). Provided behind the cavity 15 is an opening 104 in the piston 4, which opens into a tube 105 that is arranged on the rear side of the piston 4 and extends from it rearwards. This tube can be movably guided in the axial direction A through a seal 106 in the rear wall 11.

In order not to impede the function of the pneumatic system of the drive part 3, the interior of the longitudinal opening must be sealed. Besides the seal 106, which isolates the cylinder chamber 6 from the outside, the seal 20 serves for this purpose by sealing the cavity 15 and the longitudinal opening from the cylinder chamber 6.

Whereas, in the present invention, preferred embodiments of the invention are described, it is clearly pointed out that the invention is not limited to these and may also be implemented in different ways within the scope of the following claims.

The invention claimed is:

1. A percussive tool, in particular for surgical use, comprising a drive part (3) and a tool holder (25), which is linked to the drive part (3) and is arranged on a front side of the drive part (3), the drive part (3) being designed so as to exert oscillatory forces, acting in an axial direction (A), on the tool bit holder (25), characterized in that the percussive tool has a longitudinal opening provided by a through longitudinal hole extending in the axial direction (A) through the tool bit holder (25) and the drive part (3) from the front side of the percussive tool to a back side of the percussive tool for passage of a rod-shaped component, wherein the drive part (3) has a piston (4) that is driven to undergo oscillatory movements, the longitudinal opening extending through the piston (4), the tool bit holder (25) is linked to the drive part (3) by way of a drive member (17), the longitudinal opening extending through the drive member (17), wherein the drive member (17) has a enlargement (16), which is arranged in a cavity (15) in the interior of the piston (4), the longitudinal opening passing through the cavity (15) and an opening (104), behind the cavity, in the piston (4) and, in particular, the cavity (15) being sealed from a cylinder chamber (6), in which the piston (4) is situated, by means of a seal (20).

2. The percussive tool according to claim 1, wherein the tool bit holder (25) has an orifice opening (36) for receiving a tool bit end, the longitudinal opening opening into the orifice opening (36).

3. The percussive tool according to claim 1, wherein a tube (105) extends rearwards from the piston (4), wherein the longitudinal opening passes through the tube (105) and wherein, in particular, the tube (105) extends in a movable manner through a seal (106) in a rear wall (11) of the percussive tool.

4. A tool bit holder for a percussive tool in accordance with claim 1.

5. The percussive tool, in particular for surgical use, comprising
a drive part (3),
a drive member (17) linked to the drive part (3), and
a tool bit holder (25) arranged on a front side of the drive part (3) and linked to the drive member (17), the tool bit holder comprising a central body (30), a frontal terminal part (31) and rear terminal part (32), wherein the drive part (3) is designed so as to exert oscillatory forces, acting in an axial direction (A), on the tool bit holder (25) by way of the drive member (17), characterized in that the drive member (17) is linked to the tool bit holder (25) by way of a coupling (24), the coupling (24) having an outwardly tapering first part (80) and an outwardly expanding second part (81) that sits on the first part, the second part being seated on the first part under axial tension and being spread apart, and that a tension member (85) is arranged between the tool bit holder (25) and the drive member (17) for linking the parts and for producing the axial tension and wherein the tension member (85) in is the form of a coupling screw (85) extending through the coupling (24) and wherein a longitudinal opening (102) extends through the coupling screw (85 and wherein the coupling screw (85) is retained by at least one retaining element in an interlocking manner against movement and wherein the retaining element is a retaining pin (87), seated in a pin hole (88) in the rear terminal part (32) and is held by at least one pin lock (90) and the pin lock (90) has a locking element arranged in the rear terminal part (32) and held against a spring force it being possible to move the lock body out of the pin hole (88) against the spring force.

6. The percussive tool according to claim 5, wherein the coupling (24) is designed to be interlocking against rotation around the axial direction (A) and, in particular, the first part (80) has a saddle-shaped raised part.

7. The percussive tool according to claim 5, wherein the coupling (24) has at least one coupling pin (82), which extends parallel to the axial direction (A) from the drive member (17) into the terminal part (32).

8. The percussive tool according claim 5, wherein the drive member (17) extends in one piece from the coupling (24) into the drive part (3).

9. A tool bit holder for a percussive tool in accordance with claim 7.

10. The percussive tool, in particular for surgical use, comprising a drive part (3) and a tool holder (25), which is linked to the drive part (3) and is arranged on a front side of the drive part (3), the drive part (3) being designed so as to exert oscillatory forces, acting in an axial direction (A), on the tool bit holder (25), wherein the tool holder (25) has an orifice opening and a seat (3A) arranged on the orifice opening (36) for receiving a tool bit in a rotationally rigid manner, further characterized in that the seat 34 has a receiving face (40) perpendicular to the axial direction (A), from which at least four raised parts (42) project symmetrically around the orifice opening (36) frontally over the receiving face (40), between each of which space for receiving the shoulders of the tool bit remains, and the four raised parts (42) are formed such that they form symmetrical depressions (43) forming two grooves, which are mutually perpendicular and perpendicular to the axial direction A and are formed for receiving a shoulder (39) of a tool bit (25).

11. The percussive tool according to claim 10, wherein neighboring raised parts (42) are separated by a distance of approximately 10.05 mm.

12. A tool bit holder for a percussive tool in accordance with claim 10.

13. The percussive tool, in particular for surgical use, comprising a drive part (3) and a tool holder (25), which is linked to the drive part (3) and is arranged on a front side of the drive part (3), the drive part (3) being designed so as to exert oscillatory forces, acting in an axial direction (A), on the tool bit holder (25), further characterized in that the tool bit holder (25) has a central body (30) made of light metal, a front terminal part (31) made of steel, and a rear terminal part (32) made of steel, and wherein, in the tool bit holder (25), is arranged in the central body (30), a holding mechanism (50) for holding in place the tool bit engaged in the central body (30) through an orifice opening (36) and wherein a steel jacket (63) is arranged between the holding mechanism (50) and the central body (50), and wherein the holding mechanism (50) has a holding element (52), which can move transverse to the longitudinal axis against a spring force.

14. The percussive tool according to claim 13, wherein the central body (30) primarily consists of at least one of aluminum magnesium and titanium.

15. The percussive tool according to claim 13, wherein the front terminal part (31) has a seat for receiving a tool bit in a rotationally rigid manner.

16. The percussive tool according to claim 13, wherein the holding mechanism is arranged in the central body (30) and wherein the holding mechanism (50) is retained against the spring force by a pin (54), which is arranged in a blind hole (55) in the central body (30), the blind hold (55) opening into a partition between the central body (30) and the front terminal part (31) in such a way that the pin (54) is trapped in the blind hole (55) when the front terminal part (31) is mounted.

17. A tool bit holder for a percussive tool in accordance with claim 13.

* * * * *